United States Patent [19]

Fouré

[11] 4,329,279

[45] May 11, 1982

[54] ORGANOSTANNIC STABILIZING COMPOSITIONS FOR VINYL HALIDE RESINS

[75] Inventor: Michel Fouré, Artix, France

[73] Assignee: Societe Nationale Elf Aquitaine, France

[21] Appl. No.: 151,638

[22] Filed: May 20, 1980

[30] Foreign Application Priority Data

May 23, 1979 [FR] France ................... 79 13109

[51] Int. Cl.$^3$ ............................................. C07F 7/22
[52] U.S. Cl. ............................ 524/180; 260/410.6; 260/429.7; 524/181; 524/567
[58] Field of Search ................ 260/429.7, 45.75 S

[56] References Cited

U.S. PATENT DOCUMENTS

| | | | |
|---|---|---|---|
| 4,080,362 | 3/1978 | Hutton et al. | 260/429.7 |
| 4,080,363 | 3/1978 | Hutton et al. | 260/429.7 |
| 4,104,292 | 8/1978 | Dworkin et al. | 260/429.7 |
| 4,105,684 | 8/1978 | Hutton et al. | 260/429.7 |
| 4,124,618 | 11/1978 | Dworkin et al. | 260/429.7 X |
| 4,167,520 | 9/1979 | Burley | 260/429.7 |
| 4,188,334 | 2/1980 | Wehner et al. | 260/429.7 |
| 4,234,501 | 11/1980 | Groenenboom et al. | 260/429.7 |

*Primary Examiner*—Helen M. S. Sneed
*Attorney, Agent, or Firm*—Ostrolenk, Faber, Gerb & Soffen

[57] ABSTRACT

New organostannic stabilizers for vinyl halide resins, and particularly for polyvinylchloride. These compounds can be obtained by the reaction of organostannic trihalides with mercapto alkyl esters and they can be used alone or in combination with other known stabilizers.

13 Claims, No Drawings

ORGANOSTANNIC STABILIZING COMPOSITIONS FOR VINYL HALIDE RESINS

BACKGROUND OF THE DISCLOSURE

The present invention relates to new organostannic stabilizers for vinyl halide resins and their method of preparation.

The new organostannic stabilizers are of the formula:

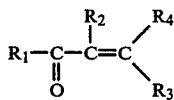

in which $R_1'$ is the radical of an olefin compound containing a carbonyl group adjacent to the carbon-carbon double bond. Such olefin compounds are of the formula:

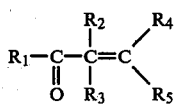 (1)

in which $R_2$, $R_3$, $R_4$ represent hydrogen or an alkyl hydrocarbon radical containing 1 to 3 carbon atoms and $R_1$ is an alkyl group, a hydroxyl or a hydrocarbon group containing oxygen.

These olefine compounds include methyl, ethyl, or hexyl acrylate, acrylic acid, vinyl methyl ketone, and methyl crotonate. The group

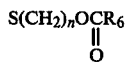

is the radical of mercapto alkyl ester in which the mercapto group is contained in the alcohol radical of the ester, $R_6$ being an alkyl containing 1 to 18 carbon atoms; it may belong to any aliphatic mono- or di-acid; however, the preferred esters are derived from fatty acids, in particular caprylic, pelargonic, capric, undeconoic, lauric, myristic, palmitic, stearic acid and isostearic acid or mixtures of such acids.

"n" may be equal to 2, 3 or 4; one of the $CH_2$'s may be substituted by a hydroxyl group.

These new organostannic stabilizers

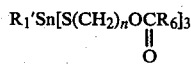

are obtained by the reaction of organostannic trihalides $R_1'SnHal_3$ and mercaptoalkyl esters

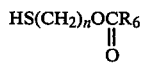

that is to say esters in which the mercapto group is present in the alkyl radical of the ester and not in the acid radical, as in the case of certain products described in the prior art. It is surprising to note that due to this difference in the position of the —SH group, the activity of the new organostannic esters is imparted with remarkable effectiveness. In addition, there are the advantages of ease of preparation and of purification of the substances.

The stannic trihalides themselves can be obtained either in accordance with the process described in French Pat. No. 2,285,392 or, preferably, in accordance with the process described in the French Patent Application filed on this date by the Societe Nationale Elf Aquitaine, by the action of a stannous compound on an excess of an olefin compound of formula (1) in the presence of a hydracid, the mixture being free of solvent.

These new organostannic compounds have excellent properties for the stabilization of the vinyl halide resins, particularly polyvinylchloride; they make it possible to reduce the discoloration of the vinyl halide resins during heating, without interfering with control of viscosity.

They may be used either alone or in combination with the other stannic stabilizers known from the prior art; in particular, they give excellent results in combination with the dialkyl tins such as, for instance, di-n-butyl tin bis(isooctylmercaptoacetate) $Bu_2Sn(SCH_2CO_2i.C_8H_{17})_2$ in proportions varying between 5 and 95% of monoalkyl tin to 95 to 5% of dialkyl tin.

The resins which contain a halogen to which the invention applies may be homopolymers, such as polyvinylchloride, polyvinylidene chloride, polychlorotrifluoroethylene, polytetrafluoroethylene, polychloroether, polydichlorostyrene, etc., copolymers such as polyvinylchlorides modified by methylene and/or propylene, by acrylonitrile butadiene styrene, ethylene vinyl acetate and the like.

The new stabilizers may be incorporated in the resin after the polymerization but before the drying of the polymer or else at the time of the use of the latter; their proportion may vary within wide limits, in particular from 0.1 to 5% of the weight of the resin, and particularly from 0.5 to 2%.

The invention is illustrated—not by way of limitation—by the following examples:

EXAMPLE 1

Preparation of the stabilizers:

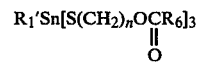

Preparation of (3-methoxycarboxyl-ethyl)-tris (2-palmitoyloxy-ethylthio) tin

A 500 ml round-bottom flask provided with an agitator and a thermometer is placed on a heating bath; 7.8 g (0.025 mol) of $Cl_3SnCH_2CH_2COOCH_3$, 23.7 g (0.075 mol) of mercaptoethylpalmitate and 300 ml of dry hexane are introduced into the flask. It is heated until the products are completely dissolved, whereupon it is allowed to return to a temperature of 40° C. 7.6 g (0.075 mol) of triethylamine are then added drop by drop, whereupon heating is effected for three hours at 40° C. The triethylamine hydrochloride precipitate is filtered; in the cooled filtrate, 18.5 g of a white solid crystallize; it is analyzed and characterized as being

Analysis: $C_{58}H_{112}O_8S_3Sn$: 1151 Calculated: C: 60.47%; H: 9.73%; S: 8.34%; Cl: 0, Found: C: 60.89%; H: 9.91%; S: 8.32%; Cl: 0.

From the mother liquors, there is recovered an additional amount (5.1 g) of the desired product.

EXAMPLE 2

Preparation of (3-methoxycarbonylethyl)-tris-(2-myristoloxyethylthio) tin 21.8 g (0.07 mol) of (trichloro)(3-methoxycarbonylethyl) tin, 61 g (0.21 mol) of mercaptoethylmyristate and 450 ml of dry hexane are introduced into a 1 liter round-bottom flask placed on a heating bath and provided with an agitator, a thermometer and a dropping funnel. Heating is effected until complete solution is obtained, whereupon the temperature is allowed to drop to 40° C. and 21.3 g (0.21 mol) of triethylamine dissolved in 50 ml of hexane are added drop by drop; heating is then effected for 3 hours at 40° C. 29 g (namely 100% of the theoretical amount) of tris ethylamine hydrochloride formed are filtered off. The filtrate is cooled to 0° C. By filtration, there is obtained 63.2 g of white solid, which crystallizes. This product is characterized as having the formula:

$$CH_3OCOCH_2CH_2Sn[S(CH_2)_2OCOC_{13}H_{27}]_3$$

Analysis: $C_{52}H_{100}O_8S_3Sn$: 1067, Calculated: C: 58.48%; H: 9.35%; S: 9.00%, Found: C: 58.46%; H: 9.58%; S: 9.04%.

EXAMPLE 3

Preparation of (3-methoxycarbonylethyl)-tris-(2-stearoyloxyethylthio) tin

The manner of operation is identical to that described in Example 2. 15.6 g (0.05 mol) of $Cl_3SnCH_2$—$CH_2CO_2CH_3$ and 51.6 g (0.15 mol) of mercaptoethyl stearate are introduced into the flask. At the end of the treatment, there is obtained 47.5 g, namely a yield of 77%, of a white solid the melting point of which is 57° C. This product is characterized by spectroscopy as being the desired product:

$$CH_3OCOCH_2CH_2Sn(SCH_2CH_2OCOC_{17}H_{35})_3$$

EXAMPLE 4

Stabilizing effect of compounds of type

 (Stabilizer B)

In this example, samples of polyvinylchloride, stabilized with the compound prepared in Example 1, are subjected to discoloration tests upon heating. For this purpose, there are mixed together at 185° C., on a roller mixer, a composition comprising:
- 100 parts by weight of polyvinylchloride known under the trade name LACOVYL S 071 S of a viscosity coefficient K of 56
- 0.5 part of "E" wax which constitutes the external lubricant
- 0.5 part of stabilizer prepared in Example 1.

Under these conditions, there is obtained a resin having an excellent initial color. The discoloration of the resin is observed and the time at the end of which the commencement of discoloration has taken place is 9 to 10 minutes and that after which the browning of the sample appears is 14 minutes. This result is close to that observed with the corresponding butyl tin compound $BuSn(SCH_2CH_2OCOC_{15}H_{31})_3$.

EXAMPLE 5

Stabilizing effect of a formulation consisting of a stabilizer of type

 (Stabilizer B)

combined with a dialkyl tin (Stabilizer C).

Stabilizers of the above type with $R_6=C_{13}, C_{15}, C_{17}$ are tested jointly with di-n-butyl tin-bis(isooctylmercaptoacetate).

The formulation comprises:

| | |
|---|---|
| Polyvinylchloride | 100 parts by weight |
| Stabilizer B | 0.1 part |
| Stabilizer C | 0.2 part |
| "E" wax | 0.5 part |

The results as a function of the nature of the radical R are given in Table I below and compared with the formulation which included only Stabilizer C.

TABLE I

| | | Appearance of the color (time in minutes) | | |
|---|---|---|---|---|
| Formulation | | Very light Yellow | Yellow | Brown(decomposition) |
| C:0.3p (reference) | 1 | 2 | 3–4 | 12 |
| B:0.1p + C, 0.2p ($B:R_6^+ = C_{17}H_{35}$) | 2 | 3–4 | 7–8 | 18 |
| B:0.1p + C, 0.2p ($B:R_6^1 = C_{15}H_{31}$) | 3 | 5–6 | 8–9 | 22 |
| B:0.1p + C, 0.2p ($B:R_6^+ = C_{13}H_{27}$) | 4 | 4–5 | 7–8 | 25 |

It follows from this table that formulations 2-3-4 have a synergistic effect as compared with formulation 1, both from the standpoint of the initial color and from the standpoint of the long-term stability.

EXAMPLE 6

This example indicates the favorable effect of formulations 2-3-4 of Example 5 on the viscosity of polyvinylchloride. The determinations set forth were carried out by means of a Brabender apparatus, which makes it possible to record the change with time of the mixing torque of the resin at a given temperature.

The formulation used is as follows:

| | |
|---|---|
| Polyvinylchloride | 100 parts by weight |
| $CaCO_3$ | 3 parts by weight |
| $TiO_2$ | 1 part by weight |
| "E" wax | 0.8 part by weight |
| Stabilizing system | |
| $BuSn(SCH_2CO_2C_8H_{17})_2$ | 0.75 part by weight |
| $CH_3OCO(CH_2)_2Sn[S(CH_2)_2OCOC_{15}H_{31}]_3$ | 0.72 part by weight |

One operates at 200° C. with a speed of rotation of the rotor of the mixer of 60 rpm.

The curves obtained indicate a plateau of about 16 minutes with a torque of 1.6 m.kg.

What I claim is:

1. New monoorganic tris-thioalkyl tin compounds of the general formula:

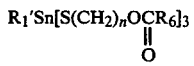

in which R' is the radical of an olefin:

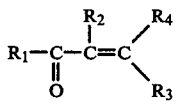 (1)

in which $R_2$, $R_3$, and $R_4$ represent hydrogen or an alkyl hydrocarbon radical containing from 1 to 3 carbon atoms and $R_1$ represents an alkyl group, a hydroxy or a hydrocarbon group containing oxygen, and the three

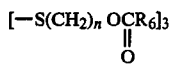

groups are the radical of a mercapto alkyl ester in which the mercapto group is contained in the alcohol radical of the ester, $R_6$ is an alkyl containing from 1 to 18 carbon atoms, n is equal to 2, 3 or 4; one of the methylenes optionally substituted by a hydroxyl group.

2. Organostannic compounds according to claim 1, characterized by the fact that the $R_6$ is a radical of an aliphatic mono- or di-acid.

3. Organostannic compounds according to claims 1 or 2, characterized by the fact that $R_6$ is a radical of caprylic, pelargonic, capric, undecanoic, lauric, myristic, palmitic, stearic, or isostearic acid or a mixture of such acids.

4. A stabilizer composition for polyvinyl halides, characterized by the fact that the composition contains at least one compound according to claim 1 or 3 in combination with a different stannic stabilizer.

5. A stabilizer composition according to claim 4 wherein said stannic stabilizer is a dialkyl tin.

6. A stabilizer composition according to claim 5 wherein said dialkyl tin is di-n-butyl tin bis(isooctylmercapto acetate).

7. Organostannic compounds according to claim 1 selected from the group consisting of (3-methoxycarboxylethyl)-tris(2-palmitoyloxy-ethylthio) tin, (3-methoxycarbonylethyl)-tris-(2-myristoloxyethylthio) tin and (3-methoxycarbonylethyl)-tris-(2-stearoyloxyethylthio) tin.

8. A polyvinyl halide composition containing a stabilizing amount of at least one organostannic compound according to claim 1.

9. A polyvinyl halide composition containing a stabilizing amount of at least one organostannic compound according to claim 2.

10. A polyvinyl halide composition containing a stabilizing amount of an organostannic compound according to claim 3.

11. A polyvinyl chloride composition containing a stabilizing amount of a mixture of an organostannic compound according to claim 1 and a different stannic stabilizer.

12. A polyvinyl chloride composition according to claim 11 characterized by the fact that $R_6$ is a radical of an aliphatic mono- or di-acid and said other stannic stabilizer is a dialkyl tin.

13. A polyvinyl chloride composition according to claim 12 characterized in that said organostannic stabilizer is selected from the group consisting of (3-methoxycarboxylethyl)-tris-(2-palmitoyloxy-ethylthio) tin, (3-methoxycarbonylethyl)-tris-(2-myristoloxyethylthio) tin and (3-methoxycarbonylethyl)-tris-(2-stearoyloxyethylthio) tin and said dialkyl tin is di-n-butyl-tin-bis-(isooctylmercapotacetate).

* * * * *